(12) United States Patent
Kasprzak, II et al.

(10) Patent No.: US 10,034,788 B2
(45) Date of Patent: Jul. 31, 2018

(54) STENT GRAFT ADAPTOR

(71) Applicant: Cook Medical Technologies LLC, Bloomington, IN (US)

(72) Inventors: Piotr Miroslaw Kasprzak, II, Regensburg (DE); Werner Dieter Ducke, Eight Mile Plains (AU); David Ernest Hartley, Wannanup (AU); Blayne A. Roeder, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 127 days.

(21) Appl. No.: 14/843,271

(22) Filed: Sep. 2, 2015

(65) Prior Publication Data
US 2016/0030218 A1    Feb. 4, 2016

Related U.S. Application Data

(63) Continuation of application No. 13/798,532, filed on Mar. 13, 2013, now Pat. No. 9,149,372.

(30) Foreign Application Priority Data

May 2, 2012 (AU) ................ 2012202565

(51) Int. Cl.
*A61F 2/966* (2013.01)
*A61F 2/962* (2013.01)
(Continued)

(52) U.S. Cl.
CPC .............. *A61F 2/962* (2013.01); *A61F 2/07* (2013.01); *A61F 2/848* (2013.01); *A61F 2/89* (2013.01);
(Continued)

(58) Field of Classification Search
CPC .. A61F 2/962; A61F 2/89; A61F 2/848; A61F 2/966; A61F 2/07;
(Continued)

(56) References Cited

U.S. PATENT DOCUMENTS

| 4,728,328 A | 3/1988 | Hughes et al. |
| 6,287,335 B1 | 9/2001 | Drasler et al. |

(Continued)

FOREIGN PATENT DOCUMENTS

WO    WO 03/053283 A1    7/2003

OTHER PUBLICATIONS

Examiner's First Exam Report for corresponding AU 2012202565 dated May 23, 2012, 2 pages.
(Continued)

*Primary Examiner* — Corrine McDermott
*Assistant Examiner* — Tin Nguyen
(74) *Attorney, Agent, or Firm* — Brinks Gilson & Lione

(57) ABSTRACT

A stent graft adaptor has an outer graft tube and an inner graft tube with the inner graft tube substantially concentric with and within the outer graft tube. A joining member extends between the inner tube and the outer tube. The joining member can be a continuous fold of graft material extending from a proximal end of the outer tube to a proximal end of the inner tube. The inner tube has at least one self expanding stent on an outer surface thereof and the outer graft tube has at least one self expanding stent on an inner surface. The outer surface of the outer tube provides a sealing surface to engage against the wall of a vessel and the inner tube provides a sealing surface to engage with a corresponding sealing surface of a stent graft deployed through it. The outer sealing surface can include barbs.

16 Claims, 7 Drawing Sheets

(51) Int. Cl.
*A61F 2/07* (2013.01)
*A61F 2/848* (2013.01)
*A61F 2/89* (2013.01)
*A61F 2/95* (2013.01)
*A61F 2/06* (2013.01)

(52) U.S. Cl.
CPC ........ *A61F 2/966* (2013.01); *A61F 2002/061* (2013.01); *A61F 2002/077* (2013.01); *A61F 2002/8483* (2013.01); *A61F 2002/9511* (2013.01); *A61F 2250/006* (2013.01)

(58) Field of Classification Search
CPC ........ A61F 2002/8483; A61F 2002/061; A61F 2002/077; A61F 2002/9511; A61F 2250/006
See application file for complete search history.

(56) References Cited

U.S. PATENT DOCUMENTS

| | | | |
|---|---|---|---|
| 6,451,050 B1 | 9/2002 | Rudakov et al. | |
| 7,766,959 B2 | 8/2010 | DiMatteo et al. | |
| 2002/0052643 A1 | 5/2002 | Wholey et al. | |
| 2003/0236567 A1* | 12/2003 | Elliot | A61F 2/07 623/1.13 |
| 2006/0217796 A1 | 9/2006 | DiMatteo et al. | |
| 2007/0191930 A1 | 8/2007 | Lucas et al. | |
| 2008/0288044 A1* | 11/2008 | Osborne | A61F 2/07 623/1.13 |
| 2009/0210047 A1 | 8/2009 | Amplatz et al. | |
| 2009/0270971 A1* | 10/2009 | Xiao | A61F 2/07 623/1.14 |
| 2010/0256754 A1 | 10/2010 | Styrc | |
| 2011/0029059 A1 | 2/2011 | Christiansen et al. | |

OTHER PUBLICATIONS

European Search Report and Written Opinion for corresponding EP 13275106 dated Sep. 20, 2013, 5 pages.
Examiner's Examination Report for corresponding EP 13275106 dated Aug. 22, 2016, 4 pages.

* cited by examiner

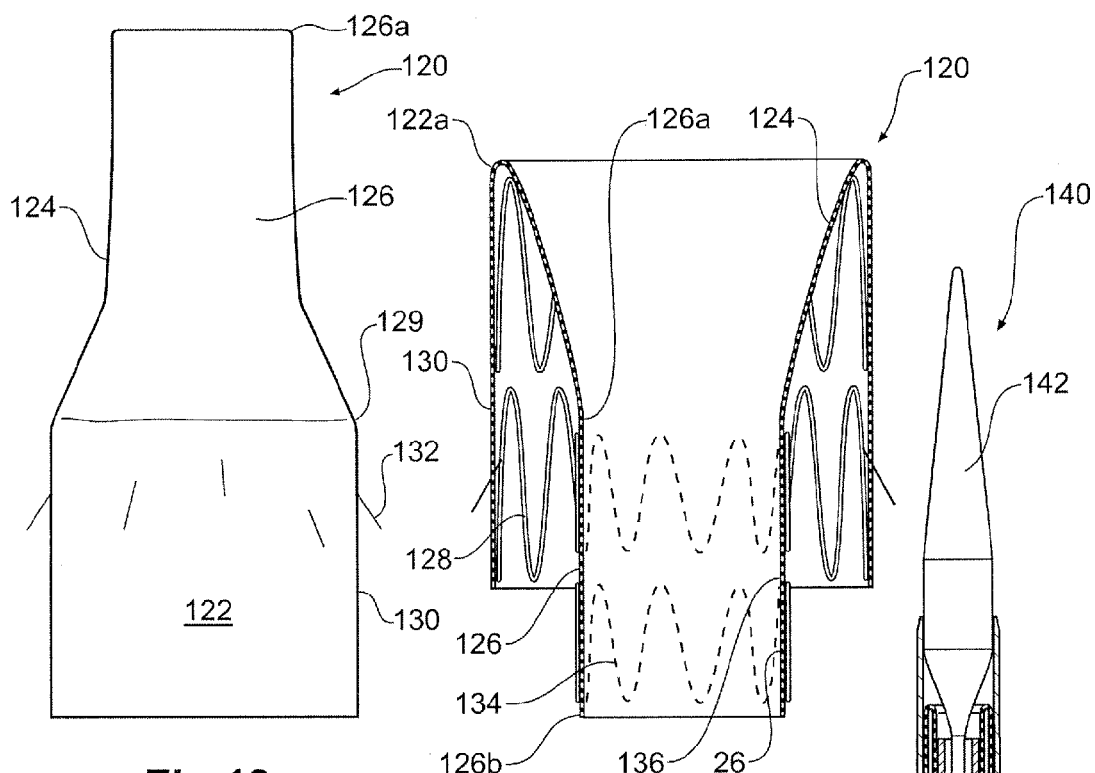
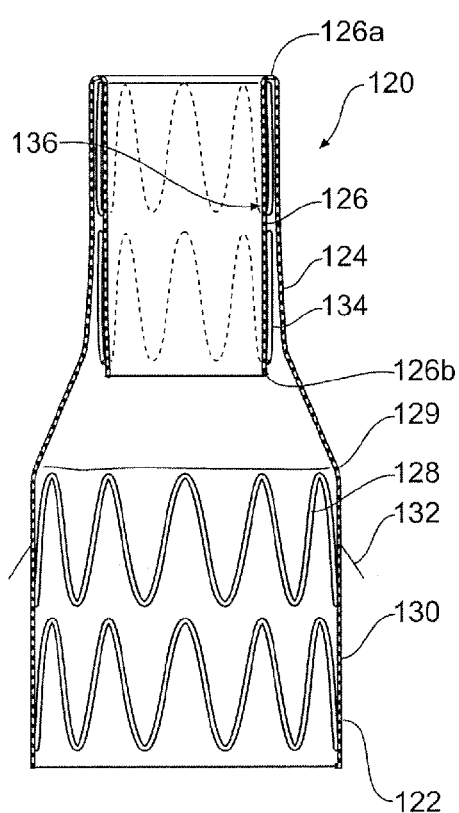
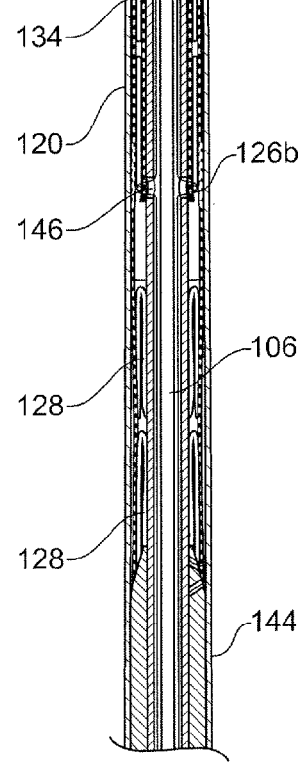
Fig 12
Fig 14
Fig 13
Fig 15

STENT GRAFT ADAPTOR

RELATED APPLICATIONS

The patent application is a continuation of application Ser. No. 13/798,532, filed Mar. 13, 2013, which claims the benefit of priority to Australian Patent Application No. 2012202565, filed May 2, 2012, and entitled "Stent Graft Adaptor," the entire contents of each of which are incorporated herein by reference.

BACKGROUND

1. Technical Field

This invention relates to a medical device and more particularly to a medical device for introduction by endovascular techniques.

2. Background

Stent grafts are used for endovascular introduction into the vasculature of a patient. Generally these stent grafts are used to bridge a defect or damaged portion of the vasculature by providing an alternate flow path. Generally the stent graft is placed so that its ends engage on to non-diseased vasculature either side of the damaged portion. Where there are branch vessels extending from the vasculature, side branches can be provided but a side vessel is very small it is usually not practical to provide a side branch.

In one particular situation when stent grafts are placed into the thoracic region of the aorta, there may be occluded one or more intercostal arteries either because a stent graft has a landing zone where there is an intercostal artery or the intercostal artery exists in the damaged area.

Occlusion of intercostal arteries can cause temporary or permanent paraplegia and it is an object of this invention to alleviate or prevent the risk of such paraplegia.

BRIEF SUMMARY

In one form therefore, although this may not necessarily be the broadest or only form, the invention is said to reside in a stent graft adaptor comprising an outer graft tube and an inner graft tube, the outer graft tube being substantially concentric with the inner graft tube, the outer graft tube and the inner graft tube defining an annular region therebetween and a joining member extending between the inner graft tube and the outer graft tube and the joining member closing off the annular region to prevent fluid flow through the annular region.

Preferably an outer surface of the outer graft tube comprises a sealing surface to engage against the wall of a vessel and the inner tube comprises a sealing surface to engage with a corresponding sealing surface of a stent graft deployed therethrough.

Preferably the inner graft tube comprises at least one self expanding stent on an outer surface thereof and the outer graft tube comprises at least one self expanding stent on an inner surface thereof.

Preferably the joining member comprises a continuous fold of graft material extending from a first end of the outer tube to a first end of the inner tube.

Alternatively the joining member can comprise an annular portion of graft material fastened to and extending from an inner surface of the outer graft tube to and fastened to an outer surface of the inner graft tube. In such a situation the annular portion of graft material can extend between the outer tube and the inner tube at a location between the ends of the outer tube and the inner tube.

Preferably the stent graft adaptor comprises barbs extending outwards from the outer graft tube in use to engage with the wall of a vessel into which the adaptor is deployed.

Preferably the outer graft tube comprises a diameter of up to 46 mm to fit in most descending aortas and the inner graft tube comprises a diameter of 32 mm to mate with an interference fit into a 34 mm thoracoabdominal device and the outer graft tube comprises a length of about 50 mm.

In an alternate form the invention comprises a stent graft adaptor comprising an outer graft tube and an inner graft tube, the outer graft tube being substantially concentric with the inner graft tube, the inner graft tube and the inner graft tube defining an annular region therebetween and a joining member extending between the inner graft tube and the outer graft tube and the joining member closing off the annular region to prevent fluid flow through the annular region, the joining member comprising a continuous fold of graft material extending from a proximal end of the outer tube to a proximal end of the inner tube, the inner graft tube comprising at least one self expanding stent on an outer surface thereof and the outer graft tube comprising at least one self expanding stent on an inner surface thereof, whereby an outer surface of the outer graft tube provides a sealing surface to engage against the wall of a vessel and the inner tube provides a sealing surface to engage with a corresponding sealing surface of a stent graft deployed therethrough.

In an alternate form the invention comprises a stent graft adaptor in combination with an introducer,
the introducer comprising a pusher, the pusher comprising a proximal end to be introduced into a patient and a distal end, a dilator at the proximal end of the pusher, a first temporary retention arrangement on the pusher distal of the dilator,
the stent graft adaptor comprising an outer graft tube and an inner graft tube, the outer graft tube being substantially concentric with the inner graft tube, the inner graft tube having a first diameter and a proximal end and a distal end, the outer graft tube having a second diameter and a proximal end and a distal end, the first diameter being smaller than the second diameter, a joining member extending between the proximal end of the inner graft tube and the proximal end of the outer graft tube, the inner graft tube comprises one self expanding stent on an outer surface thereof and the outer graft tube comprises at least one self expanding stent on an inner surface thereof, the stent on the inner graft tube being at a distal end of the inner graft tube,
the stent graft adaptor being mounted onto the introducer with the distal end of the inner tube and the stent of the inner tube retained distally of the dilator by the first temporary retention arrangement an the joining member and the outer graft tube distally thereof.

Preferably the stent graft adaptor in combination with an introducer further includes a second temporary retention arrangement distal of the first retention arrangement, the distal end of the outer tube being temporarily retained by the second temporary retention arrangement.

Preferably the stent graft adaptor in combination with an introducer further comprises barbs extending outwards from the outer graft tube in use to engage with the wall of a vessel into which the adaptor is deployed.

It will be seen that by this invention there is provided an arrangement which can act as an adaptor for placement of a stent graft and which reduces the amount of landing zone necessary which can potentially give a reduction in the potential for temporary or permanent paraplegia.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

Various stent types and stent constructions may be used in the stent graft of the present invention. In general, the stents may be formed from any material and have any structure that is expandable and has sufficient radial strength to retain its shape. For example, the stents may be balloon expandable or self-expanding stents. The stents may be capable of radially contracting, radially distensible and/or deformable. Self-expanding stents include those that have a spring-like action which causes the stent to radially expand, or stents which expand due to the memory properties of the stent material for a particular configuration at a certain temperature. A preferred self-expanding stent is the Z-STENT®, available from Cook, Incorporated, Bloomington, Ind. USA.

Any suitable stent material is contemplated including, but not limited to, stainless steel, platinum, gold, titanium, Nitinol™ and other nickel-titanium alloys, MP35N® and other nickel-cobalt alloys, Cobalt L-605™ and other cobalt-chromium alloys, other biocompatible metals, metal-alloys, as well as polymeric stents.

This then generally describes the invention but to assist with understanding reference will now be made to the accompanying drawings which show preferred embodiments of the invention.

BRIEF DESCRIPTION OF THE DRAWINGS

FIGS. 12 and 13 show views of an alternative embodiment of a stent graft adaptor according to the present invention in a configuration as it would be loaded on to a delivery device;

FIG. 14 shows a longitudinal cross section of the embodiment of FIGS. 12 and 13 in its deployed and ready to use configuration; and FIG. 15 shows a longitudinal cross section of the embodiment of FIGS. 12 and 13 loaded on to a delivery device and constrained with a sheath.

DETAILED DESCRIPTION OF THE DRAWINGS AND THE PRESENTLY PREFERRED EMBODIMENTS

Figures 1A, 1B:
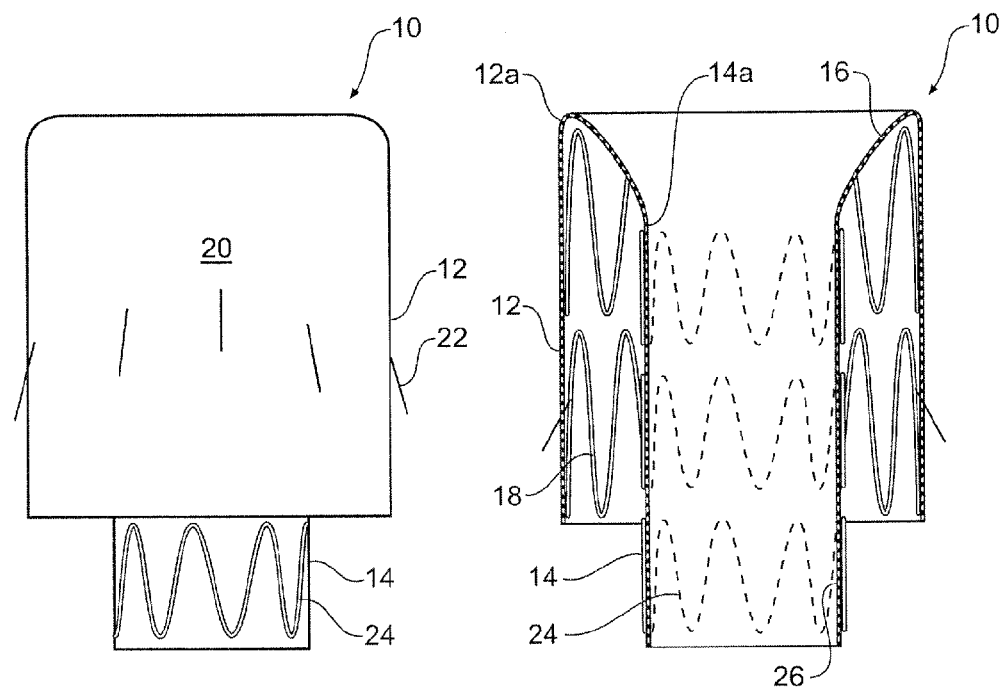
FIGS. 1A and 1B show a first embodiment of stent graft adaptor according to the present invention.

Now looking at the drawings and in particular FIGS. 1A and 1B, it will be seen that a stent graft adaptor 10 according to one embodiment of the invention comprises an outer graft tube 12 and an inner graft tube 14. The inner graft tube 14 is substantially concentric with the outer graft tube and substantially within the outer graft tube. A connecting member 16 joins the outer graft tube from the top 12a of the outer graft tube to the top 14a of the inner graft tube. Preferably the inner graft tube 14, the outer graft tube 12 and the connecting member are formed from a single piece of biocompatible graft material.

The outer graft tube has at least one self-expanding zigzag stent 18 on its inner surface so that it presents an outer sealing surface 20. Barbs 22 fastened to the stent 18 extend out through the wall of the outer graft tube to engage in to the vasculature of a patient in use to prevent movement of the stent graft adaptor after it has been deployed into the vasculature.

The inner graft tube 14 has at least one and preferably a number of self-expanding stents 24 on its outer surface so that it presents an inner sealing surface 26. These self expanding stents can be relatively weak because all they need to do is to hold the inner tube open until a proximal end of a thoracoabdominal device or similar device is placed and expanded into it.

Figures 2A, 2B:
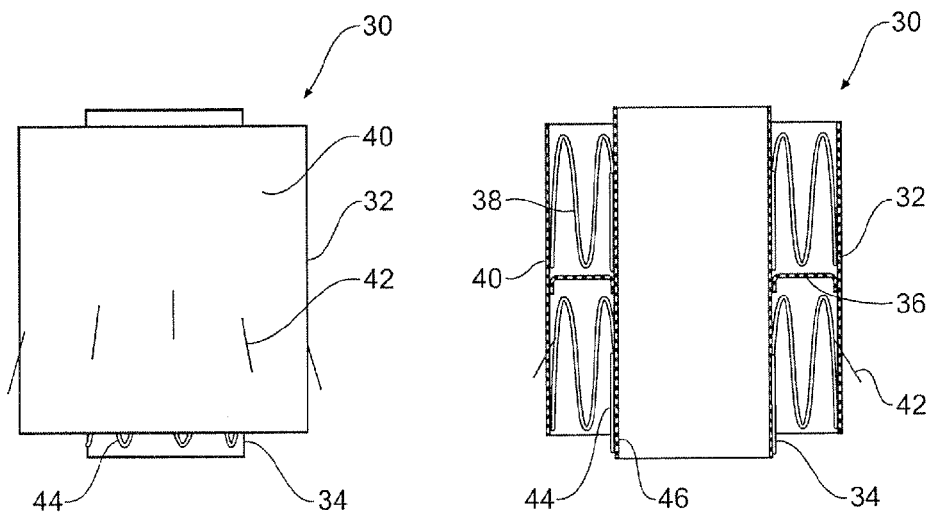
FIGS. 2A and 2B show an alternative embodiment of stent graft adaptor according to the present invention.

FIGS. 2A and 2B show an alternative embodiment of a stent graft adaptor 30 according to the present invention. In this embodiment the adaptor 30 has an outer tube 32 and an inner tube 34. The inner graft tube 34 is substantially concentric with the outer graft tube 32 and substantially within the outer graft tube 32. A connecting member 36 joins the outer graft tube with the inner graft tube. The connecting member is an annular portion of graft material fastened to and extending from an inner surface of the outer graft tube to and fastened to an outer surface of the inner graft tube. The connecting member 36 extends between the outer tube and the inner tube at a location between the ends of the outer tube and the inner tube.

The outer graft tube 32 has at least one self-expanding zigzag stent 38 on its inner surface so that it presents an outer sealing surface 40. Barbs 42 fastened to the stent 38 extend out through the wall of the outer graft tube to engage in to the vasculature of a patient in use to prevent movement of the stent graft adaptor after it has been deployed into the vasculature.

The inner graft tube 34 has at least one and preferably a number of self-expanding stents 44 on its outer surface so that it presents an inner sealing surface 46. These self expanding stents can be relatively weak because all they need to do is to hold the inner tube open until a proximal end of a thoracoabdominal device or similar device is placed and expanded into it.

The device as shown in either of FIGS. 1A and 1B or 2A and 2B is in use compressed onto a introducer device to be introduced into the vasculature of a patient. Generally the device of the present invention would be deployed first at a selected position in the vasculature to occlude as few as possible or none of the intercostal arteries and then a thoracoabdominal device deployed so that its proximal end is expanded or expands into the inner tube to provide a proximal seal for the thoracoabdominal device.

Figure 3:
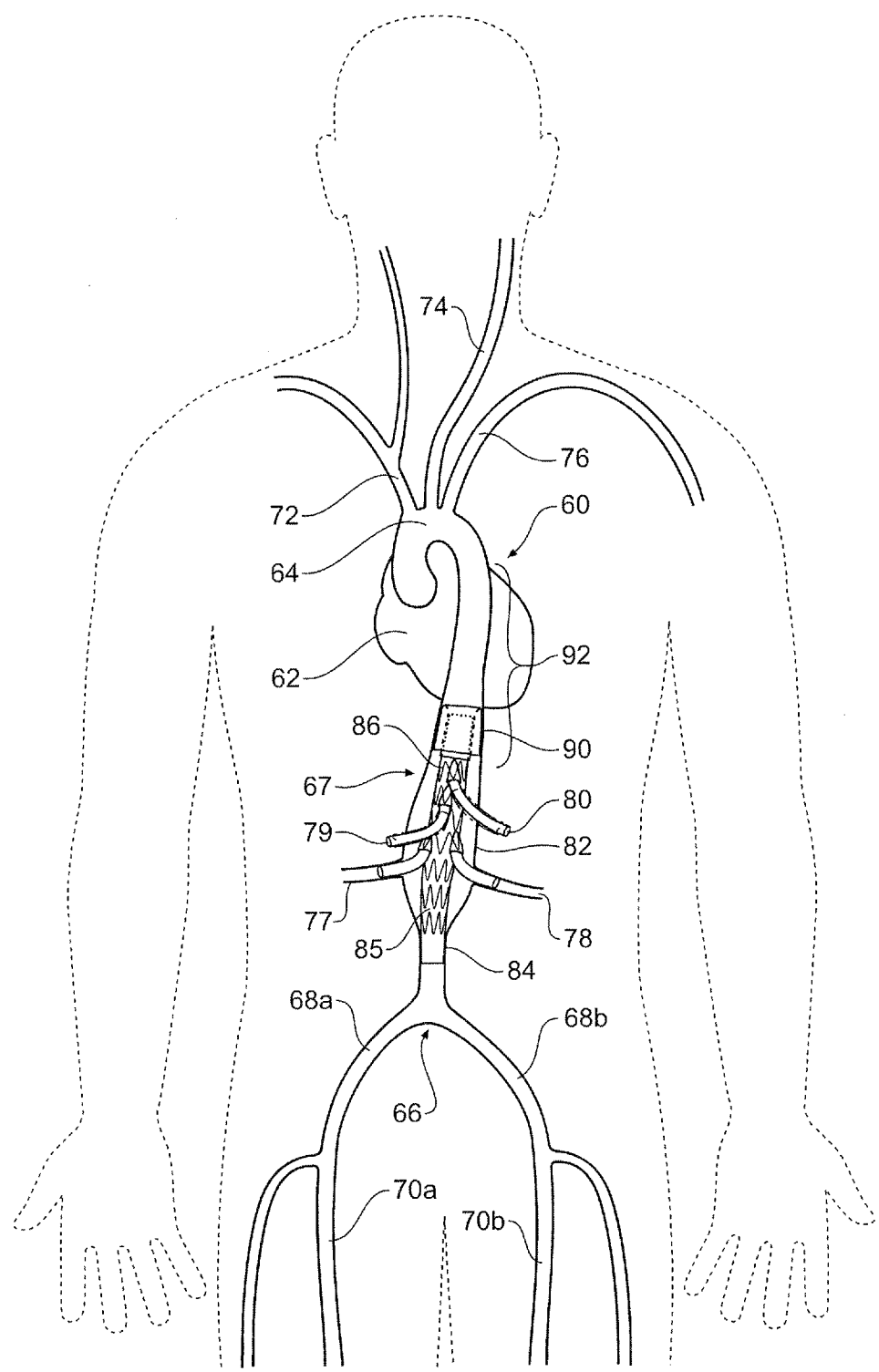
FIG. 3 shows the aortic vasculature of a patient including the placement of a thoracoabdominal stent graft and a stent graft adaptor according to the present invention.

FIG. 3 shows a schematic view of the aortic vasculature of a human body. The vasculature shown comprises an aorta 60 extending from a heart 62 over a thoracic arch 64 to an aortic bifurcation 66 via a descending aorta 67. At the aortic bifurcation iliac arteries 68a and 68b extend down to respective femoral arteries 70a and 70b. From the thoracic arch 64 the brachiocephalic artery 72, the left carotid artery 74 and the left subclavian artery 76. In the aorta there are renal arteries 77 and 78 and extending from the aorta a little above the renal arteries are the superior mesenteric artery 79 and the celiac artery 80. These four arteries can generally be referred to as the pararenal arteries. The aorta 60 is depicted with an aneurism 82 which has occurred in the region of the pararenal arteries and as illustrated, a stent graft has been deployed into the aorta with a distal landing zone 84 in a non-diseased part of the aorta adjacent to the aortic bifurcation 66 to seal the distal end of the stent graft 85. At the proximal end 86 of the stent graft 85 a stent graft adaptor 90 according to the present invention has been deployed.

Figure 4:
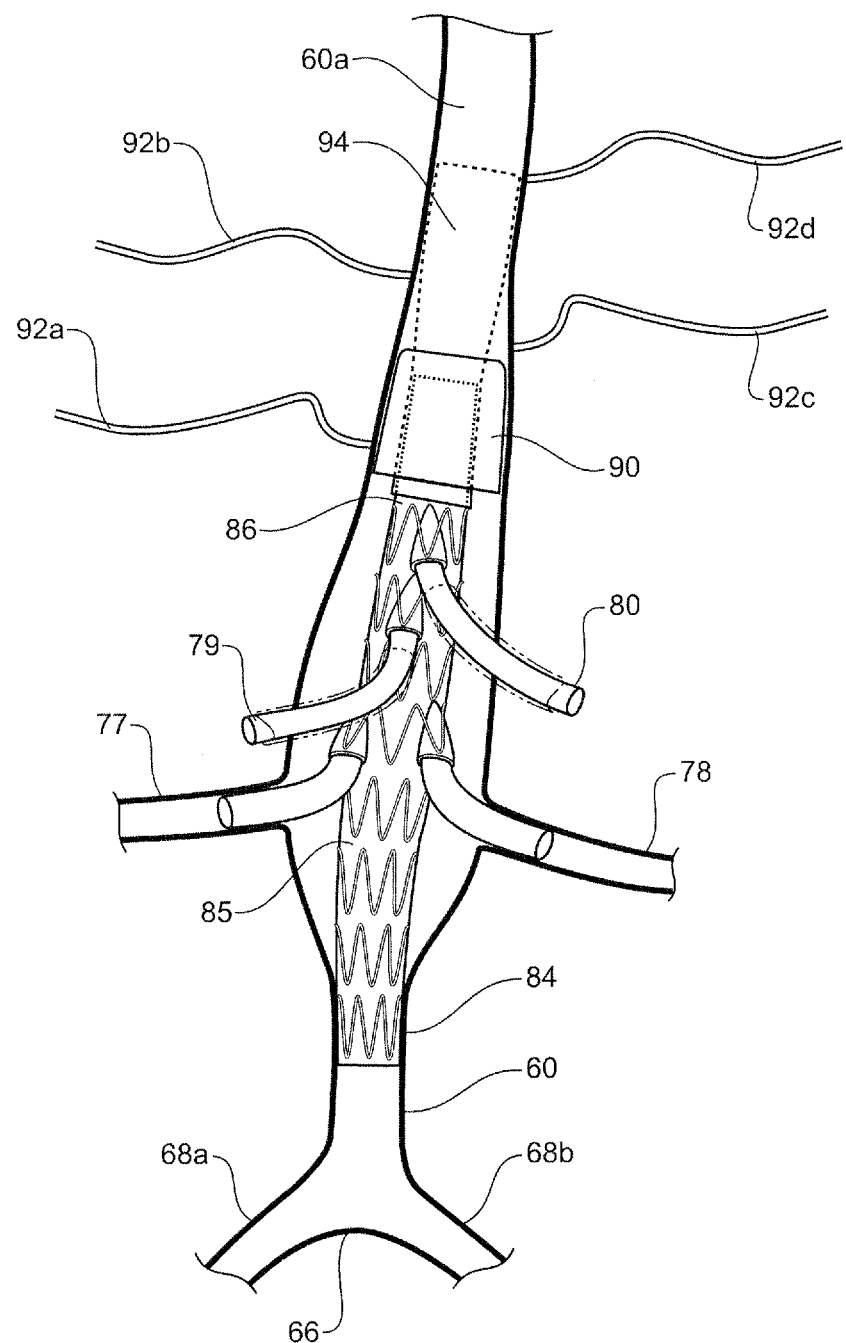
FIG. 4 shows detail of the thoracoabdominal vasculature as shown in FIG. 3.

The intercostal arteries which can cause problems with paraplegia are in the region indicated by the bracket 92 and as shown in more detail in FIG. 4.

FIG. 4 shows detail of the thoracoabdominal region shown in FIG. 3. The intercostal arteries in this region are shown as 92a to 92d.

It can be seen that the stent graft 85 has a diameter at its proximal end 86 of about 34 to 36 mm which is a smaller diameter than the diameter of the vasculature in this region and normally there would be placed a further stent graft extending further up the descending aorta 66. Such a stent graft is shown in part by the dotted lines 94.

As can be seen in FIG. 4 the placement of the adaptor 90 has caused occlusion of the intercostal artery 92a but not occlusion of the intercostal arteries 92b, 92c or 92d. If an alternative stent graft such as shown by the dotted lines 94 in FIG. 4 had been placed without essentially overlapping inner and outer tubes to act as an adaptor, then at least three intercostal arteries 92a, 92b and 92c would have been occluded and perhaps 92d as well depending on the size of the stent graft 94 and this would have considerably added to the risk of paraplegia.

Figure 5:
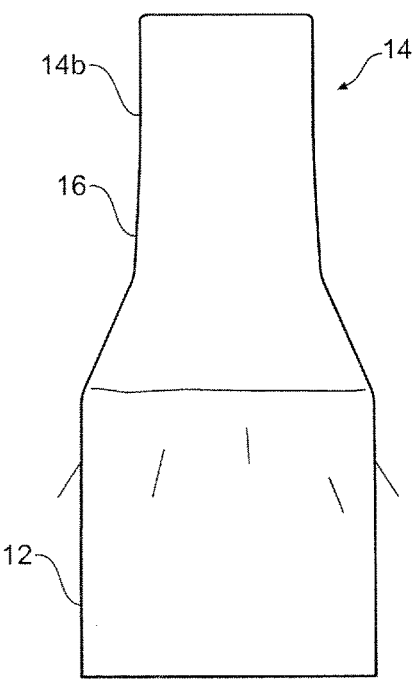
FIGS. 5 and 6 show views of an alternative embodiment of a stent graft adaptor according to the present invention in a configuration as it would be loaded on to a delivery device.
Figure 6:
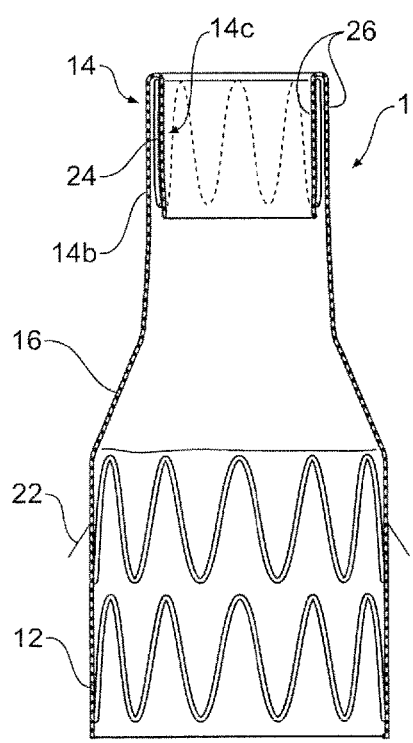
Figure 7:
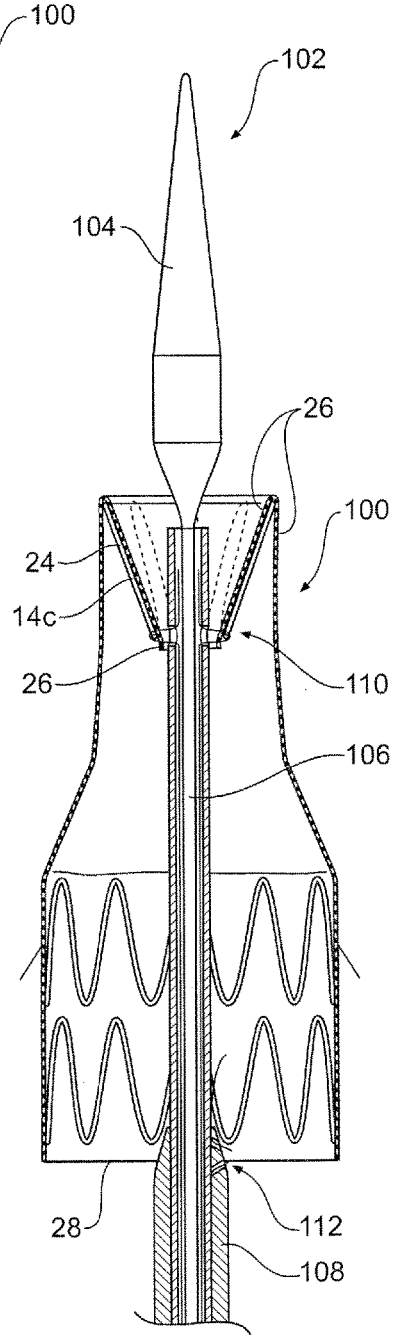
FIG. 7 shows the embodiment of FIGS. 5 and 6 loaded on to a delivery device.

FIGS. 5 and 6 show an alternative embodiment of a stent graft adaptor 100 of the present invention which is substantially the same as the embodiment shown in FIGS. 1A and 1B but is depicted in FIGS. 5 and 6 in a condition ready for mounting on an introducer device for deployment into the vasculature of a patient. In this embodiment the same reference numerals will be used as those in FIGS. 1A and 1B.

In the ready to deploy configuration shown in FIGS. 5 and 6 the stent graft adaptor 100 has an outer graft tube 12 is in substantially the same configuration as shown in FIGS. 1A and 1B but the connection member 16 extends away from the outer tube 12 and the inner tube 14 is partially inverted so that there is an outer portion 14b and an inner portion 14c of the inner tubular portion 14. The stents 18 on the outer tubular portion are in substantially the same positions as shown in FIGS. 1A and 1B but in this variation of the embodiment there is only one stent 24 on the inner tubular portion and in the ready to deploy condition this is mounted to the inner tubular portion 14c but between the inner tubular portion 14c and the outer tubular portion 14b. Hence when the stent graft adaptor 100 is finally deployed there will be an inner sealing surface 26 which has a stent at its distal end but on the outside surface of the inner tube 14.

FIGS. 7 to 11 show the various stages of mounting the stent graft adaptor of the present invention on to a delivery device and the delivery of that device into the vasculature of a patient. Only part of the delivery device is depicted. The delivery device includes a nose cone dilator 104 mounted on to a guide wire catheter 106 which extends from a pusher 108. The stent graft adaptor 100 in its ready to deploy condition is mounted on to the delivery device so that the distal end 26 of the inner portion of the inner tube 14c and the stent 24 is retained by a retention arrangement 110 just distal of the nose cone dilator 104. The distal end 28 of the outer tube 12 is retained to the pusher 108 by a release arrangement 112.

Figure 8:
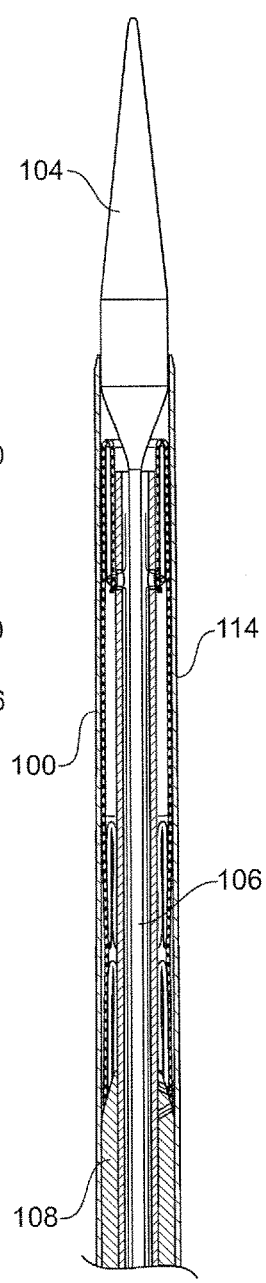
FIG. 8 shows the device of FIGS. 5 and 6 loaded on to a delivery device and constrained for endovascular delivery.

When the adaptor 100 has been so mounted a constraining sleeve 114 is placed around the device 100 and the sleeve extends forward to the nose cone dilator 104 as shown in FIG. 8.

Figures 9, 10:
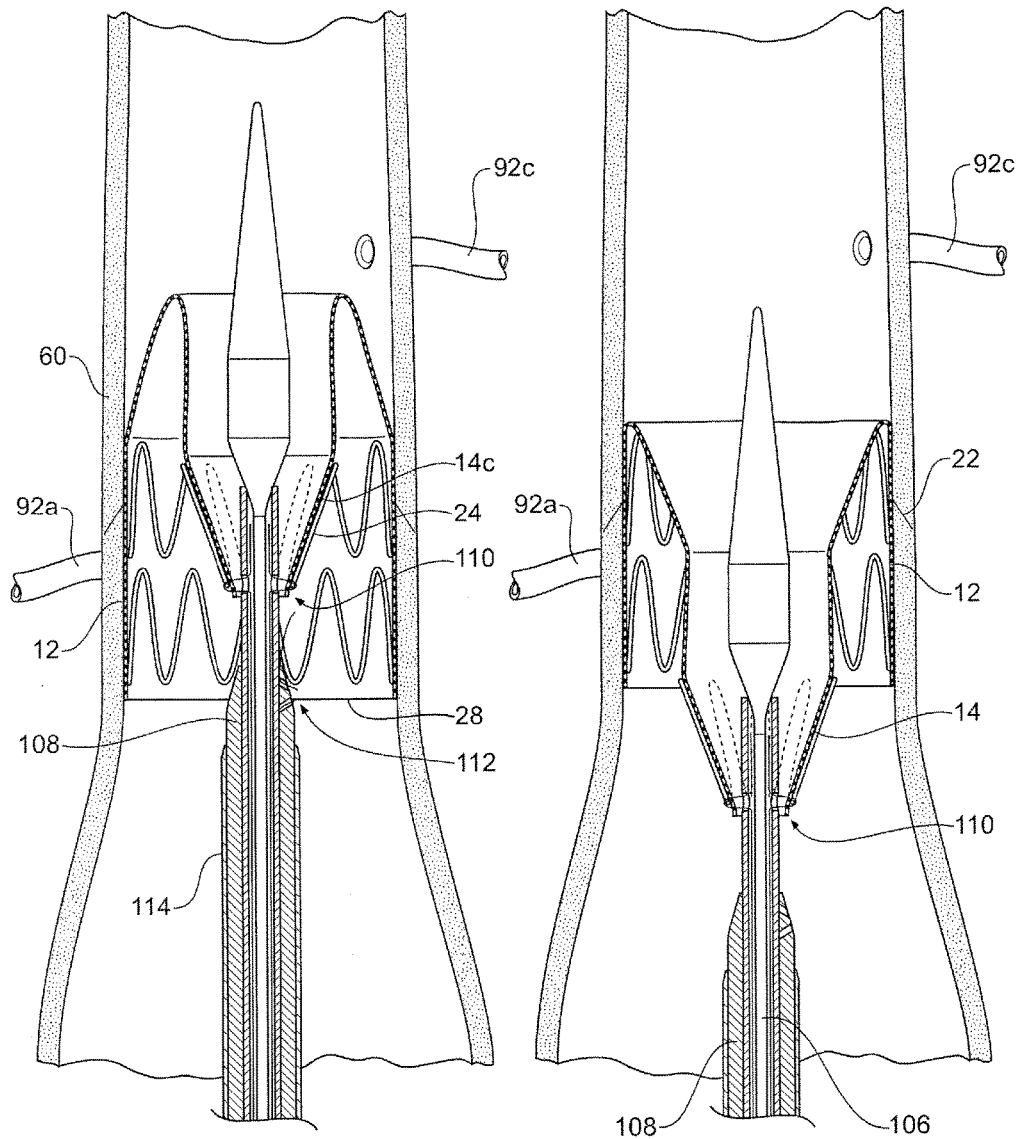
FIGS. 9 to 11 show various stages in the deployment of the device of the present invention of the embodiment shown in FIGS. 5 and 6.

As shown in FIG. 9 the introducer has been introduced into the vasculature of the patient and the sheath 114 withdrawn to release the outer tubular portion 12 so that it engages against the wall of the vasculature 60. This has occluded the intercostal artery 92a but not the intercostal artery 92c.

Still further in FIG. 9 the guide wire catheter and nose cone have been retracted with respect to the pusher 108 while the inner tubular portion 14c and stent 24 are still retained by the retention arrangement 110 and the distal end 28 is still retained by the retention arrangement 112.

As shown in FIG. 10 the distal retention arrangement has been released so that the guide wire catheter 106 and pusher 108 can be withdrawn together so that the inner tubular portion 14 is moved down to its final position. The outer tubular portion 12 remains essentially in its same position because of the barbs 22 engaging into the wall of the aorta 60.

Figure 11:
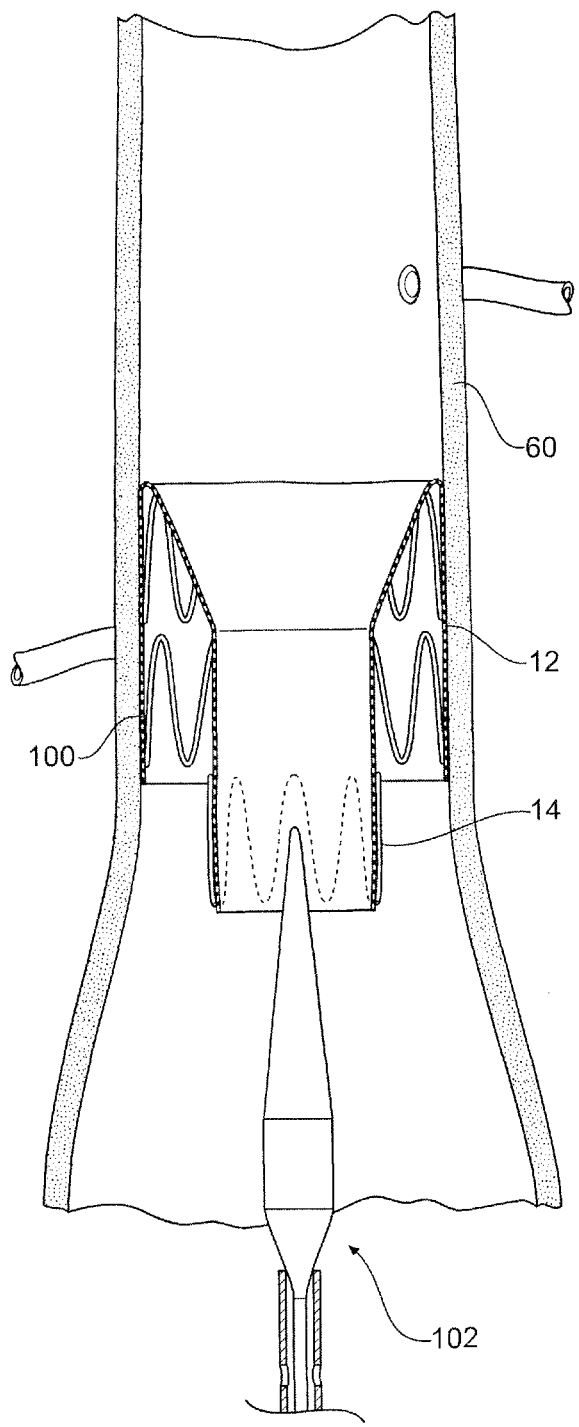

As shown in FIG. 11 the proximal retention arrangement 110 has also been released so that the stent graft adaptor 100 is completely released from the delivery device 102. The stent graft adaptor 100 is then positioned so that the outer tubular portion 12 is engaged against the wall of the aorta 60 and the inner tubular portion 14 is substantially concentric with and substantially within the outer tubular portion 12.

FIGS. 12, 13 and 14 show an alternative embodiment of a stent graft adaptor of the present invention and FIG. 15 shows the embodiment of FIGS. 12 to 14 loaded on to a delivery device and constrained within a sheath.

In the deployment configuration shown in FIGS. 12 and 13 and deployed configuration shown in FIG. 14 the stent graft adaptor 120 has an outer graft tube 122 a connection member 124 and an inner graft tube 126. The inner graft tube 126 is substantially concentric with and in use is within the outer graft tube 122. The connecting member 124 joins the top 122a of outer graft tube 122 from the top 126a of the inner graft tube 126. Preferably the inner graft tube 126, the outer graft tube 122 and the connecting member 124 are formed from a single piece of a relatively lightweight biocompatible graft material such as Dacron.

The outer graft tube has two self-expanding zigzag stents 128 on its inner surface so that it presents a smooth outer sealing surface 130. Barbs 132 fastened to the stent 128 extend out through the wall of the outer graft tube to engage into the vasculature of a patient in use to prevent movement of the stent graft adaptor after it has been deployed into the vasculature.

The inner graft tube 126 has two self-expanding stents 134 on its outer surface so that it presents a smooth inner sealing surface 136. These self expanding stents can be relatively weak because all they need to do is to hold the inner tube open until a proximal end of a thoracoabdominal device or similar device is placed and expanded into it.

In the ready to deploy configuration shown as in FIGS. 12 and 13 the connecting member 124 is not within the outer graft tube 122 so that when the device is constrained into a delivery device as shown in FIG. 15 the stents 134 on the inner graft tube 126 are not aligned with the stents 128 on the outer graft tube 122 so that the device as a whole can be constrained within a relatively low diameter delivery device 140. The delivery device 140 has a proximal dilator 142 and a sheath 144 which constrains the stent graft adaptor 120. The stent graft adaptor 120 is retained onto the delivery device at least at the distal end 126b to the delivery device by a restraint arrangement 146.

In the delivery process the delivery device is deployed into the artery, for instance, of a patient until the outer graft tube 122 is in a desired longitudinal location and then the sheath 144 is withdrawn which allows the outer graft tube 122 to expand to the wall of the artery under the action of the stent 128. At this stage the stents 134 are still constrained and held onto the delivery device by the restraint arrangement 146 and the delivery device can then be withdrawn slightly until the inner graft tube is in the relative position as shown in FIG. 14 at which time the restraint arrangement 146 can be released. The delivery device can then be withdrawn. The stent graft adaptor is then available to deploy the proximal end of a thoracoabdominal device or similar device into it.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A stent graft delivery assembly comprising:
a delivery device including a proximal end, a distal end, a nose cone dilator at the proximal end, the nose cone dilator having a proximal tip and a distal end, and a guidewire catheter extending from the distal end of the delivery device to at least the nose cone dilator;
a stent graft mounted at least partially over the guidewire catheter the stent graft comprising a tube of graft material and having a proximal end, a distal end and at least one stent attached to the tube of graft material, the tube of graft material having a proximal end, a proximal portion having a first diameter, a proximal portion inner lumen, a distal end, a distal end portion having a second diameter, a distal portion inner lumen in fluid communication with the proximal portion inner lumen;
wherein the graft material of the proximal portion is at least partially inverted into the lumen of the proximal portion to form an outer proximal tube portion and an inner proximal tube portion of graft material disposed within the outer proximal tube portion, the inner proximal tube portion having an edge of graft material disposed distal of the proximal end of the stent graft; and
wherein, in a delivery configuration, the edge is releasably attached by a first retention arrangement to the guidewire catheter distal of the proximal end of the graft material and the nose cone dilator and proximal of the distal portion of the graft material, and wherein, in a delivered configuration, the edge is released from the guidewire catheter and is the distal end of the stent graft.

2. The stent graft delivery assembly of claim 1, wherein the tube of graft material has an expanded state and a contracted state, and in the expanded state the proximal portion diameter is greater than the distal end portion diameter.

3. The stent graft delivery assembly of claim 1, further comprising a second retention arrangement releasably attaching the distal end of the stent graft to the delivery device.

4. The stent graft delivery assembly of claim 1, further comprising at least one stent attached to the distal portion of the graft material.

5. The stent graft delivery assembly of claim 4, wherein the at least one stent is attached to an inner surface of the distal portion of the graft material.

6. The stent graft delivery assembly of claim 5, further including barbs on the at least one stent.

7. The stent graft delivery assembly of claim 6, wherein the barbs extend through the graft material from the inner surface of the graft material to an outer surface.

8. The stent graft delivery assembly of claim 1, wherein the inverted portion of the proximal portion has at least one stent attached to an exterior surface of the inverted portion so as to present a smooth inner surface of the inverted portion.

9. The stent graft delivery assembly of claim 1, wherein the entire proximal portion is inverted into the lumen of the distal portion.

10. The stent graft delivery assembly of claim 1, wherein the inverted portion has a plurality of stents attached to an exterior surface of the inverted portion.

11. A stent graft delivery assembly comprising:
a delivery device including a proximal end, a distal end, a nose cone dilator at the proximal end of the delivery device, the nose cone dilator having a proximal tip and a distal end, a guidewire catheter extending from the distal end of the delivery device to at least the nose cone dilator;
a stent graft mounted at least partially over the guidewire catheter, the stent graft comprising a tube of graft material and at least one stent attached to the tube of graft material, the tube of graft material having a proximal end, a proximal portion having a first diameter in an expanded configuration, and a proximal portion inner lumen, a distal end, a distal end portion having a second diameter in an expanded configuration that is greater than the first diameter, and a distal portion inner lumen;
wherein the graft material of the proximal portion is folded over such that a portion of the proximal portion extends into its own lumen to form an outer tube and an inner tube concentric with the outer tube and connected to the outer tube by a fold of graft material at the proximal end of the stent graft, and wherein an open end of the inner tube is releasably attached to the guidewire catheter distal of the proximal end of the stent graft by a first retention arrangement in a delivery configuration; and
wherein the inner tube is longitudinally moveable within the lumen of the proximal portion and the lumen of the distal portion such that in a deployed configuration the open end is the distal end of the stent graft.

12. The stent graft delivery assembly of claim 11, further comprising a connection member between the proximal portion and the distal end portion.

13. The stent graft delivery assembly of claim 12, wherein the proximal portion, the connection member and the distal end portion are formed from a single piece of graft material.

14. The stent graft delivery assembly of claim 13, wherein the connection member comprises the fold.

15. The stent graft delivery assembly of claim 11, wherein the guidewire catheter comprises a lumen from the distal end to at least the nose cone dilator, and the first retention arrangement comprises at least one aperture in a sidewall of the guidewire catheter adjacent the open end and at least one elongate wire extending through the guidewire catheter lumen to the aperture, wherein a portion of the elongate wire extends out of the aperture to engage the open end.

16. The stent graft delivery assembly of claim 15, wherein the elongate wire re-enters the aperture and extends into the lumen of the guidewire catheter proximal of the aperture.

* * * * *